(12) United States Patent
Taylor, Jr. et al.

(10) Patent No.: US 9,841,369 B1
(45) Date of Patent: Dec. 12, 2017

(54) SYSTEM OF ANALYZING A COATING TEST

(71) Applicants: Myron E. Taylor, Jr., Brookeville, MD (US); Robert L. Hester, Rockville, MD (US)

(72) Inventors: Myron E. Taylor, Jr., Brookeville, MD (US); Robert L. Hester, Rockville, MD (US)

( * ) Notice: Subject to any disclaimer, the term of this patent is extended or adjusted under 35 U.S.C. 154(b) by 0 days.

(21) Appl. No.: 15/276,666

(22) Filed: Sep. 26, 2016

Related U.S. Application Data

(63) Continuation-in-part of application No. 15/015,005, filed on Feb. 3, 2016.

(51) Int. Cl.
  *G01N 19/00* (2006.01)
  *G01N 19/04* (2006.01)
  *H04N 5/225* (2006.01)

(52) U.S. Cl.
  CPC .............. *G01N 19/04* (2013.01); *H04N 5/225* (2013.01)

(58) Field of Classification Search
  None
  See application file for complete search history.

(56) References Cited

U.S. PATENT DOCUMENTS

| | | | | |
|---|---|---|---|---|
| 2002/0135758 | A1* | 9/2002 | Potyrailo | C09K 11/06 356/237.2 |
| 2014/0162061 | A1* | 6/2014 | Kawakita | H01B 1/127 428/372 |
| 2014/0312247 | A1* | 10/2014 | McKee | G01N 21/6456 250/459.1 |
| 2016/0327473 | A1* | 11/2016 | Ozcan | G01N 33/1813 |

FOREIGN PATENT DOCUMENTS

WO   WO 2015108820 A1 * 7/2015 .......... G01N 33/1813

OTHER PUBLICATIONS

Kakareka, John W., et al. "A portable fluorescence camera for testing surgical specimens in the operating room: description and early evaluation." Molecular Imaging and Biology 13.5 (2011): 862-867.*
Jung, Hye-Mi, and Sukkee Um. "Electrical and thermal transport properties of vanadium oxide thin films on metallic bipolar plates for fuel cell applications." International Journal of Hydrogen Energy 38.26 (2013): 11591-11599.*
Hubner, James P., et al. "Luminescent strain-sensitive coatings." AIAA journal 42.8 (2004): 1662-1668.*
Hubner, J. P., et al. "Luminescent photoelastic coatings." Experimental Mechanics 44.4 (2004): 416-424.*

* cited by examiner

*Primary Examiner* — Vu Le
*Assistant Examiner* — Tracy Mangialaschi
(74) *Attorney, Agent, or Firm* — QuickPatents, LLC; Kevin Prince

(57) ABSTRACT

A system for analyzing a coating test on a test surface with a portable electronic device includes a hood that is at least partially open at a bottom side thereof and fixable with the portable electronic device at an opposing top side thereof. At least one lamp is fixed with an inside surface of the hood and is adapted to project light towards the open bottom side thereof. A software application is resident on a memory of the portable electronic device that directs a processor of the portable electronic device to at least a) capture an image of an original color input area (CIA) of the test surface as a reference, b) capture an image of an area of interest (AOI) of the test surface, and c) compare the AOI to the CIA to determine a percentage of the coating that has been removed in the test.

19 Claims, 4 Drawing Sheets

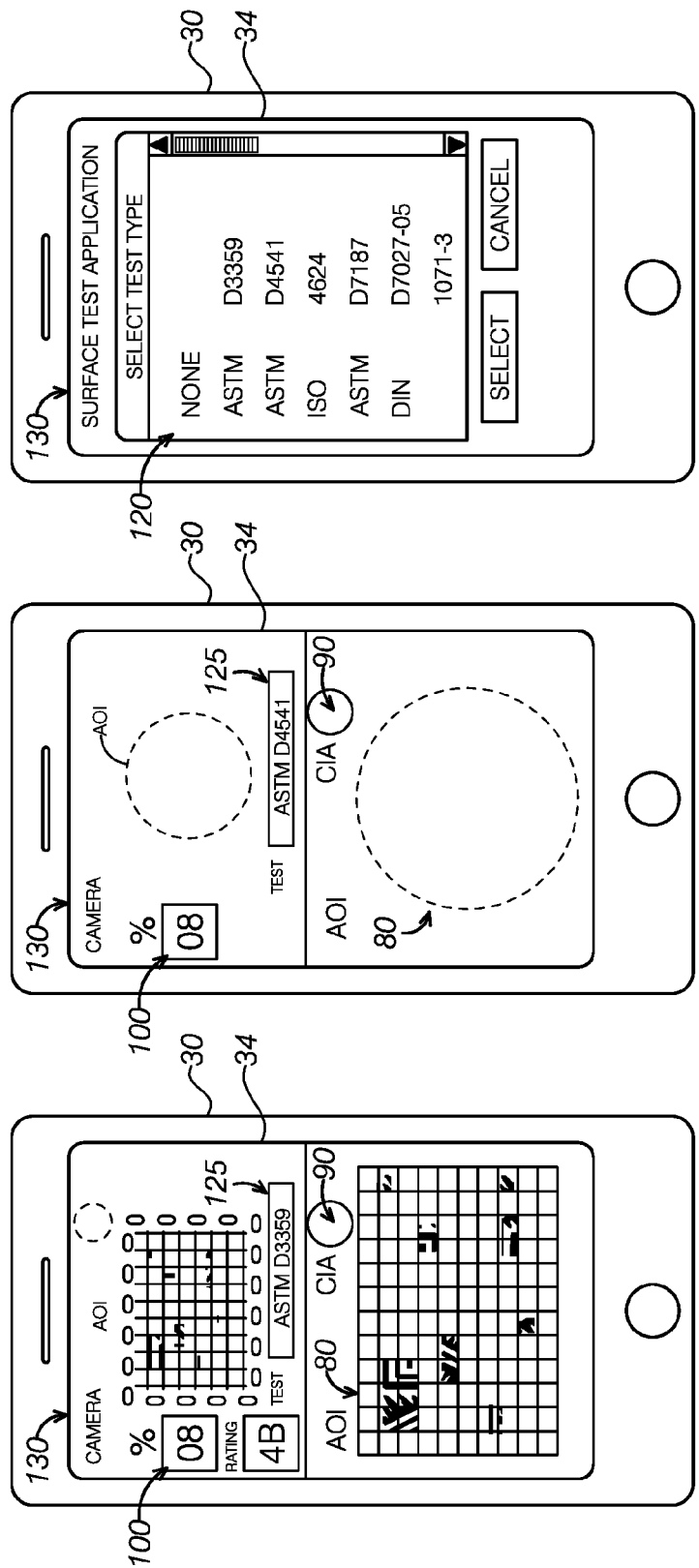

SYSTEM OF ANALYZING A COATING TEST

CROSS-REFERENCE TO RELATED APPLICATIONS

This application is a continuation-in-part of U.S. patent application Ser. No. 15/015,005, filed Feb. 3, 2016, which claims the benefit of U.S. Provisional Patent Application 62/129,892, filed on Mar. 8, 2015, both incorporated herein by reference.

STATEMENT REGARDING FEDERALLY SPONSORED RESEARCH AND DEVELOPMENT

Not Applicable.

FIELD OF THE INVENTION

This invention relates to surface testing, and more particularly to system for analyzing coating adhesion and tensile tests.

DISCUSSION OF RELATED ART

Several different types of tests are routinely conducted on coatings to determine adhesion and tensile strength characteristics. For example, a coating to be tested for adhesion is scratched through to the substrate with a special tool having multiple teeth, such as 6 to 11 teeth, first in one direction and then again at up to 90-degrees to the first scratch. At 90 degrees, most common, this produces a matrix of squares where the two scratches intersect. Subsequently a standardized adhesive tape is applied to the top of this matrix and peeled off. Some of the coating may or may not peel off depending on how well the coating is adhered to the substrate. There are multiple classifications depending on the amount of coating removed. For example, in standardized test ASTM D3359 there are six classifications (0B to 5B) each with a range of percent of coating removed within the test matrix area. If no coating was removed the result would be classified as a "5B," up to 5% a "4B," >5% to 15% a "3B," etc. to >65% a class "0B."

The results of such a test can be used to determine, for example, if a particular coating is accepted or rejected for a particular job or application. ASTM testing guidelines give visual examples in the form of drawings or photos of each class to allow the operator/technician to properly classify the coating. Determining the correct classification requires an accurate estimation of the amount of coating removed. Because the standard relies on a qualitative, visual estimation of the amount of coating removed, results can vary significantly between different technicians even when viewing the same test result. Even if different readings are within just a few percent, it could mean the difference between passing or failing a particular product. For example a 3B class would indicate that 5% to 15% of the coating was removed, while 15% to 35% would result in a 2B rating. When readings are near the limits of the two classes, score variance can increase. Further, the current method of obtaining results manually by observation and comparison is time consuming and results in questionable accuracy depending on the technician's expertise.

Tensile tests, such as that described in ASTM D4541, are another type of test where a method of obtaining more consistent results by analyzing a test surface would be beneficial. Currently with such tests if any of the coating is left behind in the test area an invalid test can be the result, when in fact a measurement of the size of the remaining coating could be measured to determine a more accurate test result. If, as often happens, the user accepts such a "partial pull" and considers the test good, even a slight variation in the area pulled results in a large change in the calculated tensile strength of the coating.

Therefore, there is a need for a system that provides a quick and consistent measure of the results of such coating tests. Such a needed invention would be portable and easy to set-up and use in the field. Further, such a needed invention would provide a choice of testing standards to use. The present invention accomplishes these objectives.

SUMMARY OF THE INVENTION

The present device is a system for analyzing a coating test on a test surface with a portable electronic device that has at least a camera, a memory, a processor, and a display screen. The system includes a preferably opaque hood that is open at a bottom side thereof and fixable with the portable electronic device at an opposing top side thereof.

The hood is formed such that the test surface is substantially parallel with the camera of the portable electronic device when the hood is placed onto the test surface. Preferably the hood further includes a mounting mechanism for selectively attaching the portable electronic device to the hood.

At least one lamp may be fixed with an inside surface of the hood and is adapted to project light towards the open bottom side thereof. A power source and a switch are preferably included with the hood for selectively applying power from the power source to the at least one lamp. The switch is preferably incorporated into the mounting mechanism and adapted to close when the portable electronic device is mounted to the hood.

A set of instructions, or a software application, is resident on a memory of the portable electronic device that directs a processor of the portable electronic device to at least a) capture an image of an original or adjacent color input area (CIA) of the test surface as a reference, b) capture an image of an area of interest (AOI) of the test surface, and then c) compare the AOI to the CIA to determine and display a measure, such as a percentage, of the coating that has been removed in the AOI vs. the total area of the AOI.

In use, the portable electronic device is mounted to the top side of the hood with the camera of the portable electronic device pointed towards the open bottom side of the hood. Preferably with the application running on the portable electronic device, the open bottom side of the hood is placed over the test surface so that the coating adhesion test, after being prompted, is contained within the AOI of the application display screen. The switch is closed to power the at least one lamp to uniformly illuminate the test coating adhesion test of the test surface, and the user selects after being prompted the CIA for the application to use as a reference. The CIA serves as a reference where the coating is unaltered or undamaged by the surface scratch test conducted in the coating adhesion test and encompassed by the AOI. Alternately, the CIA may be captured of the original AOI before the test is conducted, such as would be desirable with a tensile strength test, for example.

A test type from a list of test types may be selected by the user to alter the algorithm used to compare the CIA with the AOI. Images of both the CIA and the AOI are captured and compared, according to the selected test type, to determine and display on the portable electronic device a measure, such as a percentage, of the coating that has been removed in the AOI vs. the total area of the AOI. Based on the test type selected, a score based on the measure may further be displayed.

The present invention is a system that provides a quick and consistent measure of the results of such a coating adhesion test. The present invention is portable and easy to set-up and use in the field. Further, the present invention provides a choice of testing standards to use. Other features and advantages of the present invention will become apparent from the following more detailed description, taken in conjunction with the accompanying drawings, which illustrate, by way of example, the principles of the invention.

DESCRIPTION OF THE DRAWINGS

FIG. 4 is a display screen on a portable electronic device illustrating an application of the invention running thereon, the application analyzing a scratch coating adhesion test;

FIG. 5 is a display screen on the portable electronic device illustrating an application of the invention analyzing a tensile strength test; and FIG. 6 is an alternate display screen of the application.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
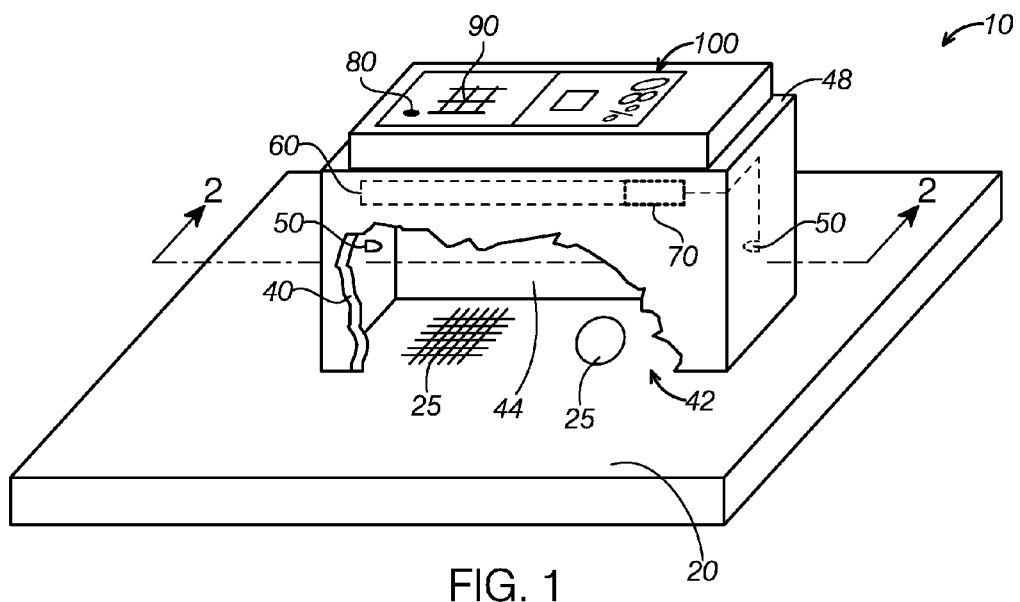
FIG. 1 is a perspective view of the invention, partially cut-away to reveal a test surface.
Figure 3A:
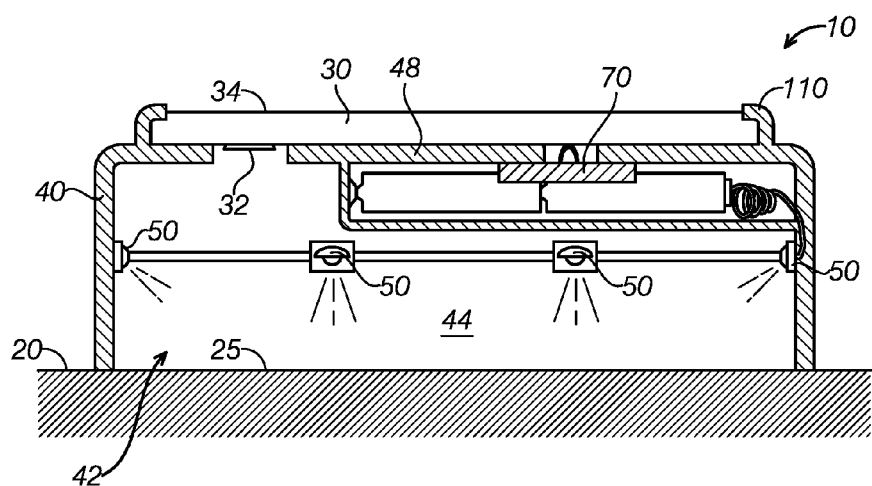
FIG. 3A is a cross-sectional view of the invention, taken along line 2-2 of FIG. 1.

FIGS. 1 and 3A illustrate a system 10 for analyzing a coating test 25 on a test surface 20 with a portable electronic device 30 that has at least a camera 32, a memory (not shown), a processor (not shown), and a display screen 34. When capturing an image of the test surface 25 with the camera 32 of the portable electronic device 30, the test surface 25 is advantageously uniformly and well lit, and the camera 32 is substantially parallel with the test surface 25. Such a coating test 25 may be, for example, a "scratch" or adhesion test that is typically performed by scratching the coating with a standard implement in a prescribed manner, such as once left-to-right, and once top-to-bottom, of a test area 25. With such a test, typically some portion of the coating that is being tested fails to adhere to the coated surface 20.

The system includes a preferably opaque hood 40 that is open at a bottom side 42 thereof and fixable with the portable electronic device 30 at an opposing top side 48 thereof. The hood 40 is formed such that the test surface 20 is substantially parallel with the camera 32 of the portable electronic device 30 when the hood 40 is placed onto the test surface 20.

The hood 40 is of a sufficient height above the test surface 25 so as to allow a clear focus of the test surface 25 with the camera 32 of the portable electronic device 30. Such focal heights or distances may vary with the camera 32, but it has been found that between 3 to 12 inches is sufficient for most such cameras 32. Preferably the hood 40 further includes a mounting mechanism 110 for selectively attaching the portable electronic device 30 to the hood 40. Such a mounting mechanism 110 may be a resilient snap-fit clamp 110, a friction-fit recess (not shown), or other type of mechanical arrangement for holding the portable electronic device 30 securely and selectively to the hood 40.

Figure 1A:
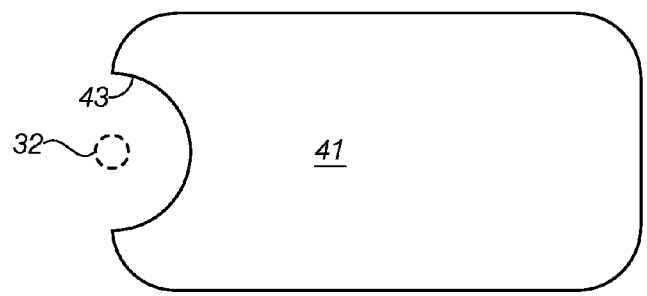
FIG. 1A is a bottom view of a hood having a base according to an exemplary embodiment of the present invention.
Figure 1B:
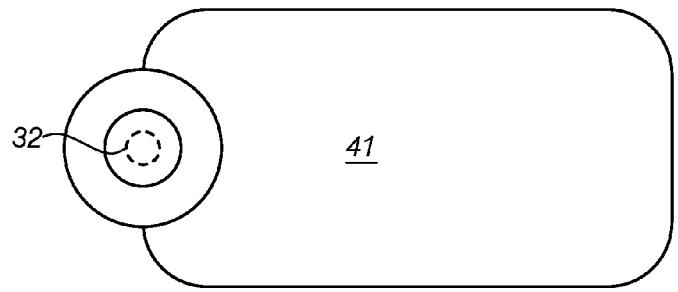
FIG. 1B is a bottom view of the hood of FIG. 1A, illustrating alignment of the base with a mask for aligning the electronic device camera lens.
Figure 3B:
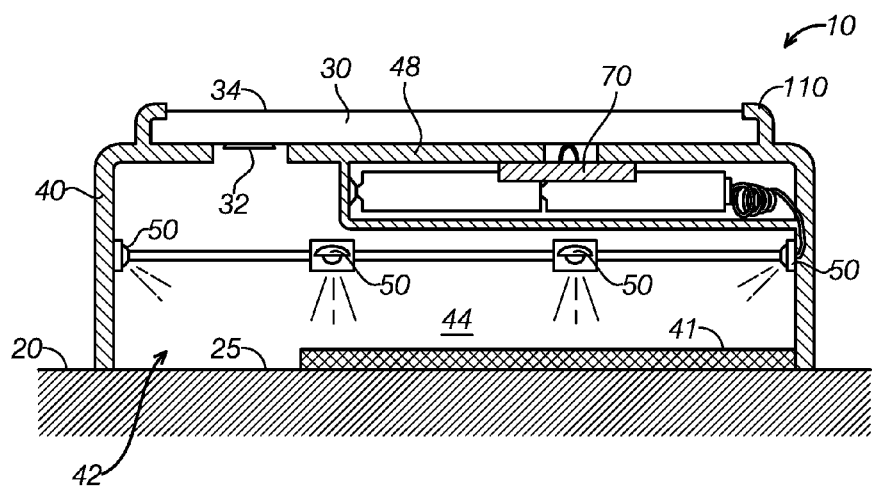
FIG. 3B is a cross-section view of the system of FIG. 1 when the hood includes a base as shown in FIG. 1A.

Referring to FIGS. 1A, 1B and 3B, in some embodiments, the hood 40 includes a base member 41 that extends partially over the open bottom side 42. A portion of an external perimeter of the base member 41 has a cut-out pattern 43 formed therein. In some embodiments, this cut-out pattern 43 is a semi-circular or arc-shaped cut-out region.

Referring additionally to FIGS. 2A through 2D, a mask 45, 47 may include an adhesive region 51 surrounding an open central region 49. The adhesive region 51 can include an adhesive, such as a removable adhesive for applying the mask 45, 47 to the test surface.

The mask 45, 47 may be placed about the test surface 25 onto which a test has been performed, with the open central region 49 surrounding an area of interest to be captured by the camera 32 of the electronic device 30. In some embodiments, the mask 45 may have a round open central region 49 for a tensile adhesion test and the mask 47 may have a rectangular open central region 49 for a scratch test, for example. Of course, other shapes of the open central region 49 are contemplated within the scope of the present invention.

An external shape of the mask 45, 47 may mate with the cut-out pattern 43 of the base member 41. Thus, as shown in FIG. 1B, when the mask is applied to the test surface 25, the base member can be easily aligned with the outside edge of the mask 45, 47 and, when so aligned, the camera 32 is properly aligned to permit the electronic device 30 to capture an image of the test region 25 through the open central region 49.

Figure 2A:
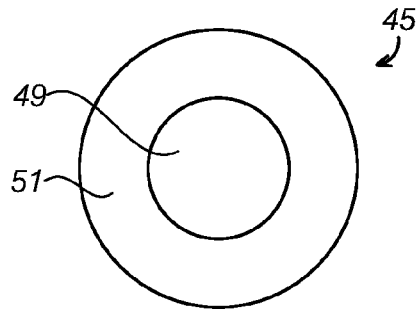
FIG. 2A is a top view of a mask configured to surround a test area according to an exemplary embodiment of the present invention.
Figure 2B:
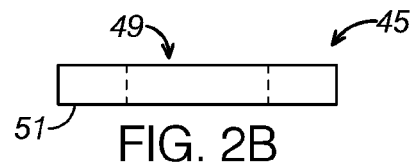
FIG. 2B is a side view of the mask of FIG. 2A.
Figure 2C:
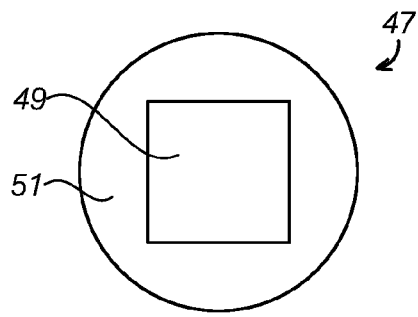
FIG. 2C is a top view of a mask configured to surround a test area according to an exemplary embodiment of the present invention.
Figure 2D:
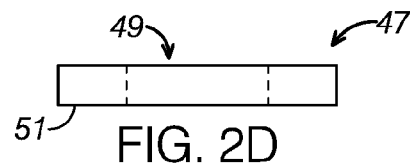
FIG. 2D is a side view of the mask of FIG. 2B.

While FIGS. 2A and 2C show the mask 45, 47 as having a circular external shape, other shapes are contemplated within the scope of the present invention, provided that the external shape of the mask 45, 47 mates with the shape of the cut-out region 43 of the base member 41. Typically, each of the masks 45, 47 will have the same external shape, allowing a single base member 41 with a single cut-out region 43 to be used with both masks 45, 47, allowing, for example, two different tests to be performed, one with each of the masks, without requiring two different hoods with different base configurations.

Figure 2E:
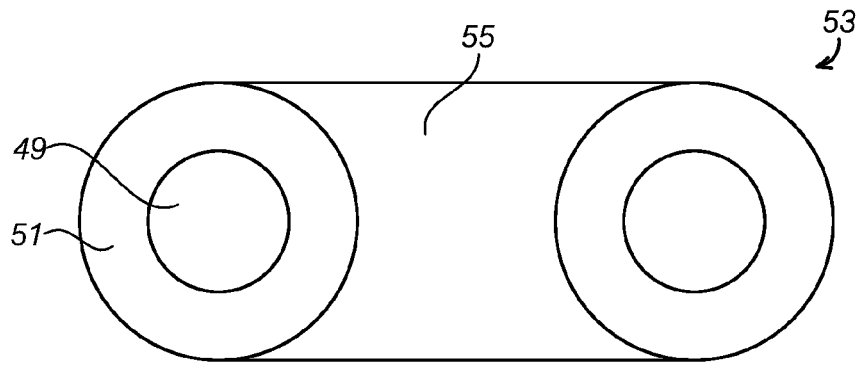
FIG. 2E is a top view of a mask configured to surround an area of interest and a color input area within a full field of view of a camera according to an exemplary embodiment of the present invention.

Referring to FIG. 2E, in some embodiments, a mask 53 can be formed from two of the above masks 45, 47, attached together, where the mask 53 includes multiple open central regions 49 surrounded by adhesive regions 51. A central linking region 55 may connect the two masks 45, 57 together. In some embodiments, the central linking region 55 may include an adhesive, similar to adhesive regions 51.

The mask 53 of FIG. 2E may allow an area of interest and a color input area, as discussed in greater detail below, to be in the full field of view of the camera 32. While a circular open central region 49 is shown for mask 53 (thus, formed from two masks 45 joined together), the mask 53 may include other shaped open central regions.

The mask 53 may have at least a portion of its outer periphery that mates with the out-out region 43 of the base member 41, thus properly aligning the camera 32 with the open central regions 49 of the mask 53.

At least one lamp 50 is fixed with an inside surface 44 of the hood 40 and is adapted to project light towards the open bottom side 42 thereof. A power source 60, such as a battery, and a switch 70 are further included with the hood 40 for selectively applying power from the power source 60 to the at least one lamp 50. The switch 70 is preferably incorporated into the mounting mechanism 110 and adapted to close when the portable electronic device 30 is mounted to the hood 40.

A set of instructions 130, also referred to herein as an "application" or just "app" 130, is resident on a memory 36 of the portable electronic device 30 that directs a processor 38 of the portable electronic device 30 to a) capture an adjacent or original image of a color input area (CIA) 80 of the test surface 20, b) capture an image of an area of interest (AOI) 90 of the test surface, and then c) compare the AOI 90 to the CIA 80 to determine and display a measure 100, such as a percentage, of the coating that has been removed in the AOI 90 vs. the total area of the AOI 90. The CIA 80 may be the same area as the AOI 90, but just captured before the test is conducted. Alternately, the CIA 80 may be an adjacent area of the test area 25.

While the hood 40 is preferably made from an opaque molded plastic material, the hood 40 could also be translucent or transparent as long as the at least one lamp 50 still are able to provide uniform illumination of the test surface. One advantage of having a transparent hood 40 is that the hood 40 and portable electronic device 30 may be easily positioned accurately over the coating adhesion test 25 of the test surface 20. On the other hand, even with an opaque hood 40 the application 130 may be coded so as to display the camera image on the display 34 before the analysis of the coating adhesion test 25 begins, which also facilitates quick and proper placement of the camera 32 over the test surface 20.

Alternately, the hood 40 may take the form of a stand (not shown) that holds the portable electronic device 20 above the test surface. In such an embodiment, a lamp (not shown) on the portable electronic device is relied upon to illuminate the test surface 25, in the event ambient light is insufficient. As such, the lamp 50 of the hood is eliminated.

In use, the portable electronic device 30 is mounted to the top side 48 of the hood 40 with the camera 32 of the portable electronic device 30 pointed towards the open bottom side 42 of the hood 40. Preferably with the application 130 running on the portable electronic device 30, the open bottom side 42 of the hood 40 is placed over the test surface 20 so that the coating adhesion test 25, after being prompted, is contained within the AOI 90 of the application 130 display screen (FIG. 4). The switch 70 is closed to power the at least one lamp 50 to uniformly illuminate the test coating adhesion test 25 of the test surface 20, and the user selects after being prompted the CIA 80 for the application 130 to use as a reference.

The CIA 80 serves as a reference where the coating is unaltered or undamaged by the surface scratch test conducted in the coating adhesion test 25 and encompassed by the AOI 90. In one embodiment, enlarged views of the CIA 80 and the AOI 90 are also displayed on the display 34 of the portable electronic device 30 (FIG. 4).

A test type 125 (FIG. 6) from a list 120 of test types 125 may be selected by the user to alter the algorithm used to compare the CIA 80 with the AOI 90. Images of both the CIA 80 and the AOI 90 are captured and compared, according to the selected test type 125, to determine and display on the portable electronic device 30 a measure 100, such as a percentage, of the coating that has been removed in the AOI 90 vs. the total area of the AOI 90. Based on the test type 125 selected, a score based on the measure 100 may further be displayed. For example, with standardized test ASTM D3359, an 8% removal of the test coating corresponds to a test score of 4B (FIG. 4).

Alternately, the image of the CIA 80 may be the test area 25 taken before the test is conducted (FIG. 5). After the test is performed, the image of the AOI 90 is captured. Such a stepwise process may be followed for tests such as tensile strength tests, for example. Alternately, with a color camera 32, the color of the test surface 25 and multiple layers of coatings can also be analyzed to determine various characteristics of each coating after a surface test is conducted.

While a particular form of the invention has been illustrated and described, it will be apparent that various modifications can be made without departing from the spirit and scope of the invention. For example, additional functions may be coded into the application 130 in addition to those described herein. Likewise, the hood 40 may take a different shape than that shown in the figures, and in fact may be more like an open stand (not shown) that holds the portable electronic device 30. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A system for analyzing a coating test on a test surface with a portable electronic device having a camera, the system comprising:
    a hood at least partially open at a bottom side and fixable with the portable electronic device at an opposing top side thereof so that the test surface is substantially parallel with the camera of the portable electronic device when the hood is placed onto the test surface, wherein the test surface contacts and extends beyond the bottom side of the hood;
    at least one lamp fixed with an inside surface of the hood operable to project light towards the bottom side, a power source and a switch further included with the hood for selectively applying power from the power source to the at least one lamp;
    a set of instructions resident on a memory of the portable electronic device that, when executed by a processor, perform steps comprising:
        a) capturing an image of a color input area (CIA) of the test surface;
        b) capturing an image of an area of interest (AOI) of the test surface;
        c) comparing the AOI to the CIA to determine and display a percentage of the coating that has been removed in the AOI vs. a total area of the AOI; and
        d) displaying both the CIA and the AOI on a display of the portable electronic device.

2. The system of claim 1, further comprising a base member partially covering the bottom side, the base member having a cut-out region along one edge thereof, the cut-out region disposed adjacent a region within a view of the camera when the portable electronic device is engaged with the hood.

3. The system of claim 2, further comprising a mask operable to be affixed to the test surface, the mask having an external shape mating with the cut-out region of the base member, the mask further having a central opening aligned with the view of the camera.

4. The system of claim 1, wherein the top side of the hood further includes a mounting mechanism for selectively attaching the portable electronic device to the hood.

5. The system of claim 4, wherein the switch is incorporated into the mounting mechanism and wherein the switch closes when the portable electronic device is mounted to the hood.

6. A method of analyzing a coating adhesion test on a test surface with a portable electronic device having a camera, the steps comprising:
    providing a hood at least partially open at a bottom side and fixable with the portable electronic device at an opposing top side thereof so that the test surface is substantially parallel with the camera of the portable electronic device when the hood is placed onto the test surface, wherein the test surface contacts and extends beyond the bottom side of the hood; at least one lamp fixed with an inside surface of the hood and operable to project light towards the open bottom side, a power source, a switch further included with the hood for selectively applying power from the power source to the at least one lamp; and a set of instructions resident on a memory of the portable electronic device;
    mounting the electronic device to the top side of the hood with the camera of the electronic device pointed towards the open bottom side of the hood;
    placing the bottom side of the hood over the test surface;
    closing the switch to power the at least one lamp to illuminate the test surface;
    capturing an image of a color input area (CIA) of the test surface;
    capturing an image of an area of interest (AOI) of the test surface; and
    comparing the AOI to the CIA to determine and display, on the portable electronic device, the AOI and the CIA as well as a percentage of the coating that has been removed in the AOI vs. a total area of the AOI.

7. The method of claim 6, further comprising:
    applying a mask to the test surface, the mask having an open central region, wherein the AOI is positioned within the open central region, the mask having an outer periphery shape; and
    aligning a base member of the hood with the mask so that a cut-out region of the base member mates with the outer periphery shape of the mask, wherein
    the aligning step positions the camera of the portable electronic device with the AOI positioned within the open central region of the mask.

8. The method of claim 7, further comprising:
    applying a second mask to the test surface, the mask having an open central region, wherein the CIA is positioned within the open central region, the mask having an outer periphery shape; and aligning the base member of the hood with the mask so that the cut-out region of the base member mates with the outer periphery shape of the mask, wherein the aligning step positions the camera of the portable electronic device with the CIA positioned within the open central region of the mask.

9. The method of claim 8, wherein the mask and the second mask are interconnected.

10. The method of claim 6, further including the steps:

displaying on the portable electronic device a field of view of the camera;

allowing a user to ensure the test surface is within the field of view of the camera;

selecting the color input area (CIA) of the test surface within the field of view of the camera; and selecting the area of interest (AOI) of the test surface within the field of view of the camera.

11. The method of claim 6, further including the steps:

selecting a test type from a list of tests; and comparing the AOI to the CIA to determine and display on the portable electronic device a rating based on the type of test and the percentage of the coating that has been removed in the AOI vs. the total area of the AOI.

12. The method of claim 6, further including the steps:

selecting a standardized test type from a list of standardized tests; and comparing the AOI to the CIA to determine and display on the portable electronic device a rating based on the type of the selected standardized test and the percentage of the coating that has been removed in the AOI vs. the total area of the AOI.

13. The method of claim 6 further including the steps:

additionally displaying an enlarged image of the CIA separately from a full field of view of the camera; and further displaying an enlarged image of the AOI separately from the full field of view of the camera.

14. A method of analyzing a coating tensile strength test on a test surface with a portable electronic device having a camera, the steps comprising:

providing a hood at least partially open at a bottom side and fixable with the portable electronic device at an opposing top side thereof so that the test surface is substantially parallel with the camera of the portable electronic device when the hood is placed onto the test surface, wherein the test surface contacts and extends beyond the bottom side of the hood; at least one lamp fixed with an inside surface of the hood and operable to project light towards the open bottom side, a power source, a switch further included with the hood for selectively applying power from the power source to the at least one lamp; and a set of instructions resident on a memory of the portable electronic device;

mounting the electronic device to the top side of the hood with the camera of the electronic device pointed towards the bottom side of the hood;

placing the open bottom side of the hood over the test surface;

closing the switch to power the at least one lamp to illuminate the test surface;

capturing an image of a color input area (CIA) of the test surface before the test is conducted;

performing the surface test;

capturing an image of an area of interest (AOI) of the test surface; and comparing the AOI to the CIA to determine and display, on the portable electronic device, the AOI and the CIA, as well as a percentage of the coating that has been removed in the AOI vs. a total area of the AOI.

15. The method of claim 14, further comprising:

applying a mask to the test surface, the mask having an open central region, wherein the AOI is positioned within the open central region, the mask having an outer periphery shape; and aligning a base member of the hood with the mask so that a cut-out region of the base member mates with the outer periphery shape of the mask, wherein the aligning step positions the camera of the portable electronic device with the AOI positioned within the open central region of the mask.

16. The method of claim 15, further comprising:

applying a second mask to the test surface, the mask having an open central region, wherein the CIA is positioned within the open central region, the mask having an outer periphery shape; and aligning the base member of the hood with the mask so that the cut-out region of the base member mates with the outer periphery shape of the mask, wherein the aligning step positions the camera of the portable electronic device with the CIA positioned within the open central region of the mask.

17. The method of claim 16, wherein the mask and the second mask are interconnected.

18. The method of claim 14, further including the steps:

displaying on the portable electronic device a field of view of the camera;

allowing a user to ensure the test surface is within the field of view of the camera;

selecting the color input area (CIA) of the test surface within the field of view of the camera;

performing the surface test; and selecting the area of interest (AOI) of the test surface within the field of view of the camera.

19. The method of claim 14, further including the steps:

additionally displaying an enlarged image of the CIA separately from a full field of view of the camera; and further displaying an enlarged image of the AOI separately from the full field of view of the camera.

* * * * *